United States Patent [19]

Mita et al.

[11] Patent Number: 4,495,082

[45] Date of Patent: Jan. 22, 1985

[54] WATER-ABSORBENT

[75] Inventors: Akio Mita, Tokyo; Susumu Kashiwabara, Hino, both of Japan

[73] Assignee: Director-General of Agency of Industrial Science and Technology, Tokyo, Japan

[21] Appl. No.: 130,348

[22] Filed: Mar. 14, 1980

[30] Foreign Application Priority Data

Apr. 4, 1979 [JP] Japan .................................. 54-40169

[51] Int. Cl.³ .............................................. C09K 3/00
[52] U.S. Cl. .................................. 252/194; 604/375; 604/904
[58] Field of Search ................ 252/194; 128/285, 284, 128/287, 296, 290 R; 162/94, 95, 96, DIG. 7

[56] References Cited

U.S. PATENT DOCUMENTS 3,935,363  1/1976  Burkholder et al. ............... 128/284
4,190,563  2/1980  Bosley et al. ........................ 128/285

Primary Examiner—Josephine Barr
Attorney, Agent, or Firm—Birch, Stewart, Kolasch & Birch

[57] ABSTRACT

A water-absorbent excellent in water-holding capacity under pressure, which comprises a cotton-like material A manufactured by a pulping treatment of bagasse containing pith and having a lignin content of at least 5% by weight and a cotton-like fibers B having a lignin content of not greater than 5% by weight. This water-absorbent is suitable as a sanitary material for manufacturing diapers, hygienic napkins or tampons.

7 Claims, 1 Drawing Figure

WATER-ABSORBENT

BACKGROUND OF THE INVENTION

This invention relates to a water-absorbent excellent in water-holding capacity under pressure.

A substance capable of absorbing water, urine, blood and other various aqueous liquids (referred to hereinafter simply as water-absorbent) is widely used, taking advantage of its water-absorbing property, as a sanitary material for manufacturing diapers hygienic napkins or tampons. Considering the conditions, the use of water-absorbents are desirably of such a nature that they are not only excellent in their water-absorbing property but also they are satisfactory for holding the absorbed liquid, even under pressurized conditions and also the absorbed liquid is substantially retained by the material.

In the past, cotton fibers have been used as a water-absorbent for this purpose. On the other hand, cotton fibers are useful for manufacturing more valuable textile materials. Since the resource of cotton is limited, however, the use of cotton for disposable diapers or hygienic napkins or tampons is discouraged in order to conserve this natural resource. In recent years, a fibrous pulp made of wood or grass has been used as a disposable water-absorbent. However, such fibrous pulp has the drawback that its water-holding capacity is poor when pressurized or compressed. In the art of this field, therefore, it is important to develop an economical water-absorbent which is bulky in the dry state, absorbs liquids when wetted therewith and holds the absorbed liquid, even when pressurized or compressed.

BRIEF SUMMARY OF THE INVENTION

It is, therefore, an object of the present invention to provide a water-absorbent excellent in both water-absorbing property and water-holding capacity.

It is another object of this invention to provide a cheap water-absorbent useful as a raw material for manufacturing disposable diapers and hygienic napkins or tampons.

Other objects, features and advantages of this invention will become apparent from the detailed description of the invention which follows, when considered in the light of the accompanying drawing, in which:

FIG. 1 is a graph showing the water-holding capacity of the water-absorbent of the present invention under pressure in comparison with that of each ingredient thereof. In this graph, the abscissa stands stands for the load in terms of $g/cm^2$ and the ordinate for a water-holding capacity in terms of grams of water per gram of the water-absorbent.

DETAILED DESCRIPTION OF THE INVENTION

Figure 1:
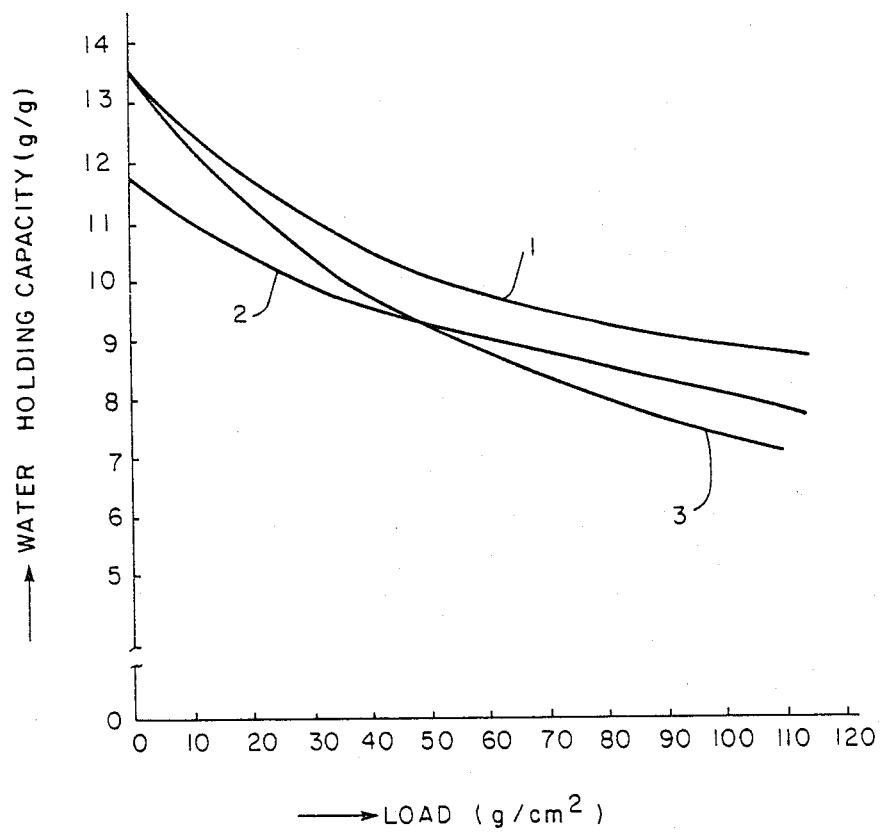

As a result of extensive research made for developing a water-absorbent excellent in both water-absorbing property and water-holding capacity, it has now been found that a mixture of a cotton-like material A manufactured by a pulping treatment of bagasse containing pith and having a lignin content of at least 5% by weight and a conventionally used cotton-like fibers B having a lignin content of not greater than 5% by weight is suitable for achieving the objects of the present invention. The present invention has been accomplished on the basis of the above finding.

The ingredient A of the water-absorbent of this invention is a cotton-like material manufactured by a pulping treatment of bagasse containing pith. When bagasse was subjected to a pulping treatment in the prior arts, spongy pith contained as a core material in bagasse was previously removed. According to the present invention, however, it is necessary to use pith-containing bagasse as the starting material since pith-free bagasse does not afford a product excellent in water-absorbing property and water-holding capacity. In this invention, it is not necessary to retain all the pith in the bagasse, since the bagasse, which is used as starting material contains at least 50% of pith, i.e. a substantial amount of pith. A preferable content of pith retained in bagasse is at least 5% by weight, especially at least 50% by weight based on the total amount of pith originally present in the bagasse.

The ingredient A of the water-absorbent is manufactured by subjecting bagasse containing pith to a pulping treatment in a conventional manner to obtain a pulp and loosening it in dry state, for example, by the aid of a crusher or shearing or impact type device, to form a very thin cotton-like material. Various known methods such as the SP process, the AP process, the KP process, the TMP process, the RGP process, the SCP process, the CGP process, the CTMP process and the SOX process are applicable as the pulping treatment in this case. The application of such pulping processes wherein a light chemical treatment followed by a mechanical treatment is carried out, such as the SCP process, the CGP process, the CTMP process or the SOX process, are preferable to obtaining a product in a high yield which has a high lignin content and is flexible and excellent in water-holding capacity. It is difficult to obtain a product having a high lignin content according to a pulping process wherein chemical treatments alone are carrried out, such as in the SP process or the KP process. On the other hand, products obtained according to a pulping process wherein mechanical treatments alone are carried out, such as the TMP process or the RGP process, tend to have stiff feeling. In pulping processes the use of alkaline chemicals affords a product having a somewhat rough feeling while the use of acidic chemicals tends to afford a product having a flexible feeling.

The nature of the ingredient A used in the water-absorbent of of the invention should be comprised of a spongy substance resulting from the pith and a fibrous substance possessing both stiffness and elasticity resulting from the co-existence of lignin and cellulose. Thus, the nature of the ingredient A should be controlled to have a lignin content within a proper range. The range recommended in this invention is 5–25% by weight, preferably 10–20% by weight. Adjustment of the lignin content can be made by suitably selecting the conditions for the pulping treatment of the bagasse. If the lignin content is too low, the stiffness of the fibrous substance will be lost so that the water once absorbed in the product will tend to be released to make the product poor in water-holding capacity. On the other hand, if the lignin content is too high, the fibrous substance in the product will be enhanced in stiffness so that the product will become stiff and poor in water-absorbing property. Thus, the lignin content of the ingredient A is desirably maintained within the above defined range. The cotton-like material manufactured from bagasse in the above described manner has a bulk density of 5–40 g/l, usually 30–40 g/l.

Ingredient B of the water-absorbent of the present invention is cotton-like fibers having a lignin content of not greater than 5% by weight. Various kinds of fibrous pulp conventionally used, such as SP, UKP, BKP or AP are utilized as the ingredient B. Broad-leaved trees in addition to needle-leaved trees are used as raw materials for such pulp. Moreover, straw, bamboo and bagasse are also utilized as raw materials for such pulp. In this invention, the ingredient B is desirably a strong pulp of generally long fibers having a low lignin content. The use of NBKP or cotton linter pulp is preferable. Ingredient B is not necessarily a single pulp but may be a mixture of at least two different pulps. Ingredient B has a bulk density of 5–40 g/l, usually 25–40 g/l.

The water-absorbent of the present invention is a mixture of the ingredients A and B. By mixing ingredient A with ingredient B, a water-absorbent excellent in both water-absorbing property and water-holding capacity can be obtained. The mixing ratio by weight of the ingredient A to the ingredient B in this case (A/B) is within the range from 95/5 to 20/80, preferably from 80/20 to 50/50.

The water-absorbent of the present invention which is composed of a mixture of ingredients A and B has an extremely high bulk density, even under pressure in the dry state. For example, a mixture of 8 g of loosened cotton-like bagasse pulp (ingredient A) and 2 g of loosened cotton-like NBKP (needle-leaved tree bleached pulp; ingredient B) has a dry bulk density of 30.3 g/l under normal pressure and dry bulk densities of 45.0 g/l and 45.5 g/l under pressures of 159.7 g/cm$^2$ and 346.0 g/cm$^2$, respectively.

The composite water-absorbent of the present invention is especially advantageous in exhibiting an extremely high water-holding capacity besides being excellent in water-absorbing property. The water absorbent of the present invention absorbs water well when wetted therewith and holds most of the absorbed water except a small amount of water squeezed out when maintained under pressure. It is surprising in this invention that the water-holding capacity of the water-absorbent is higher than an average value of the water-holding capacities of the ingredients A and B and is extremely enhanced in comparison with the water-holding capacity of each ingredient. A result of tests for evaluation of water-holding capacities of the water-absorbent and the individual ingredients is shown in FIG. 1 wherein Curve 1 shows the water-holding capacity of the water-absorbent of the present invention comprised of 80% bygasse pulp and 20% NBKP, Curve 2 shows the water-holding capacity of 100% bagasse pulp and Curve 3 shows the water-holding capacity of 100% NBKP. As is evident from the result shown in this graph, the composite water-absorbent of this invention is remarkably improved in its water-holding capacity under pressure in comparison with the cases of the individual ingredients.

The water-absorbent of the present invention can be utilized, taking advantages of its excellent water-absorbing property and water-holding capacity, for various fields of industry, especially as a sanitary material, i.e. a raw material for manufacturing paper diapers or hygienic napkins or tampons.

This invention will now be illustrated in more detail by way of examples.

EXAMPLE 1

Bagasse from which pith had not been removed was treated with a digestion liquid containing sodium sulfate and sufur dioxide whereby SOX pulp was obtained in a yield of 72%. This pulp had a lignin content of 13% and was found to retain pith therein on observation under a microscope. The pulp was loosened in dry state by the aid of an impact-type crusher to form a cotton-like material having a bulk density of 35.4 g/l which, under a pressure of 346 g/cm$^2$, had a bulk density of 75.2 g/l.

Next, NBKP produced in Canada was loosened in dry state to form cotton-like fibers having a lignin content of 0.1% or less and a bulk density of 25.2 g/l under normal pressure and a bulk density of 35.6 g/l under a pressure of 346 g/cm$^2$. The cotton-like material was mixed with the cotton-like fibers in a ratio by weight of 8:2 to obtain a water-absorbent which, in dry state, was very bulky and had a bulk density of 30.3 g/l under normal pressure and a bulk density of 45.5 g/l under a pressure of 346 g/cm$^2$.

The water-absorbing property was evaluated by dipping 10 g of this water-absorbent into water whereby 13.6 g/g of water was absorbed. When the water-absorbent in the water-absorbed state was squeezed under a pressure of 115 g/cm$^2$ to check its water-holding capacity, it was confirmed that the water-absorbent still held 8.5 g/g of water although a small amount of water was released therefrom.

EXAMPLE 2

Bagasse from which pith had not been removed was treated with an alkaline liquid and then mechanically loosened by the aid of an impact-type crusher to form bagasse CGP in a yield of 67%. This pulp had a lignin content of 14% and a bulk density of 39.8 g/l and was found to retain pith therein on observation under a microscope. The pulp was then mixed with a bleached cotton linter pulp having a bulk density of 21.2 g/l (residual lignin not detected) in a mixing ratio by weight of 5:5 to obtain a water-absorbent which had a bulk density of 37.0 g/l under a pressure of 346 g/cm$^2$.

When the water-absorbing capacity and the water-holding capacity of this water-absorbent were evaluated in the same manner as described in Example 1, the water-absorbent showed a water-absorbing capacity of 13.2 g/g under normal pressure and a water-absorbing capacity of 8.2 g/g under a pressure of 115 g/cm$^2$.

As many apparently widely different embodiments of this invention may be made without departing from the spirit and scope thereof, it is to be construed that this invention is not limited to the specific embodiments illustrated in examples except as defined in the appended claims.

What is claimed is:

1. A water-absorbent which comprises a mixture of a pulp A manufactured by a pulping treatment of bagasse containing at least 5% by weight of pith and having a lignin content of 5–25% by weight and a pulp B having a lignin content of not greater than 5% by weight, wherein the ratio by weight of pulp A to pulp B (A/B) is within the range of from 95/5 to 20/80.

2. The water-absorbent according to claim 1, wherein the pulp A has a bulk density of 5–40 g/l, preferably 30–40 g/l and the pulp B has a bulk density of 5–40 g/l, preferably 25–40 g/l.

3. The water-absorbent of claim 1 wherein the water-absorbent is a diaper.

4. The water-absorbent of claim 1 wherein the water-absorbent is a hygenic napkin.

5. The water-absorbent of claim 1 wherein the water-absorbent is a tampon.

6. A water-absorbent composite capable of absorbing and holding water, urine, blood and other aqueous liquids which comprises a mixture of pulp A manufactured by the chemical and physical treatment of bagasse containing at least 5% by weight of pith and having a lignin content of 5-25% by weight, and pulp B manufactured by the chemical and physical treatment of cotton-like fibers having a lignin content of not greater than 5% by weight, wherein the ratio by weight of pulp A to pulp B (A/B) is within the range of from 95/5 to 20/80.

7. The water-absorbent of claim 6 wherein pulp B is made from broad-leaved trees, needle-leaved trees, straw, bamboo and bagasse.

* * * * *